United States Patent [19]

Gallup

[11] Patent Number: 5,246,593
[45] Date of Patent: Sep. 21, 1993

[54] SILICA SCALE DEPOSITION CONTROL

[75] Inventor: Darrell L. Gallup, Chino, Calif.

[73] Assignee: Union Oil Company of California, Los Angeles, Calif.

[21] Appl. No.: 785,464

[22] Filed: Oct. 31, 1991

[51] Int. Cl.$^5$ ............................................. B01D 21/30
[52] U.S. Cl. ............................ 210/709; 60/641.2;
   60/641.5; 210/713; 210/714; 210/741; 210/742;
   210/747; 210/96.1; 210/143; 210/149; 364/502
[58] Field of Search ........................... 60/641.2, 641.5;
   210/709, 713, 714, 723, 726, 739, 741, 742, 747,
   96.1, 143, 149, 195.3; 364/500, 502

[56] References Cited

U.S. PATENT DOCUMENTS

| | | | |
|---|---|---|---|
| 4,500,434 | 2/1985 | Jost et al. | 210/696 |
| 4,536,845 | 8/1985 | De Vale et al. | 210/96.1 |
| 4,563,272 | 1/1986 | Yoshida et al. | 210/96.1 |
| 4,631,530 | 12/1986 | Gasper | 210/739 |
| 4,648,043 | 3/1987 | O'Leary | 210/143 |
| 4,765,912 | 8/1988 | Totten | 210/747 |
| 4,874,529 | 10/1989 | Featherstone et al. | 210/747 |
| 4,931,187 | 6/1990 | Derham et al. | 210/742 |

FOREIGN PATENT DOCUMENTS

| | | | |
|---|---|---|---|
| 2605407 | 4/1988 | France | 210/739 |
| 62-225288 | 10/1987 | Japan | 210/143 |

OTHER PUBLICATIONS

D. L. Gallup, manuscript of *Geothermal Resources Council Transactions*, 13, 241 (1989), "The Solubility of Amorphous Silica in Geothermal Brines."

Primary Examiner—Peter Hruskoci
Attorney, Agent, or Firm—Gregory F. Wirzbicki; Charles L. Hartman

[57] ABSTRACT

The concentration of amorphous silica in an aqueous solution is monitored to determine a concentration above which silica will precipitate. The precipitation concentration is data processed with a means for data processing by solving the Setchnow equation for aqueous solutions containing silica. The means for data processing generates a signal that, if need be, can be used to automatically adjust the parameters of the system to prevent silica precipitation or to carefully control the precipitation rate. An alternative embodiment provides a method for determining amorphous silica concentration, then data processing the solution to the Setchnow equation, generating a signal, and adjusting the parameters of the system. The apparatus and method of this invention are particularly useful in geothermal power plants.

35 Claims, 3 Drawing Sheets

SILICA SCALE DEPOSITION CONTROL

BACKGROUND OF THE INVENTION

1. Field of the Invention

This invention relates to methods and apparatus to control the deposition of silica scales and silica containing scales from aqueous solutions containing large concentrations of dissolved amorphous silica.

2. State of the Art

Various aqueous solutions contain large concentrations of dissolved amorphous silica, which is also sometimes described as silicic acid, $Si(OH)_4$. Such aqueous solutions are produced naturally by quartz dissolving in a subterranean geothermal fluid reservoir. As the aqueous solution is cooled, for example, in an energy producing step, the solubility of silica in the aqueous solution can be exceeded. Silica scaling on processing pipes and associated hardware results. The problem is widespread, and is present in brines processed for boiler water, in desalination plants, in the water used for plating metals, in cooling towers, and in oil and gas well applications where the scale produced from brine downhole can rapidly plug the well.

Geothermal brines are examples of such aqueous solutions that also contain significant amounts of iron. They are extracted from the earth to generate power by using steam flashed off from the brine to power a turbine. Flashing the brine to produce steam substantially lowers the temperature of the brine. A geothermal brine may or may not be saturated in amorphous silica when it is extracted from the ground, but most brines can become supersaturated in silica as the liquid cools during power generation. The presence of iron in the geothermal solution tends to complicate the scaling problem. Iron silicates form according to the following overall reaction:

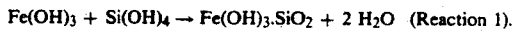

$Fe(OH)_3 + Si(OH)_4 \rightarrow Fe(OH)_3 \cdot SiO_2 + 2 H_2O$ (Reaction 1).

The precipitating scale composition tends to vary, but usually the scales have a composition described by the general empirical formula $Fe(OH)_3 \cdot SiO_2$.

The general problem of geothermal brines and the scaling they cause has been discussed in D. L. Gallup, *Geothermal Resources Council Transactions*, 13, 241 (1989) (hereinafter Gallup (1989)), which document is hereby incorporated in full by reference. In that paper use of the Setchnow equation to calculate silica solubility was discussed. One could not previously calculate silica solubility of naturally occurring brines because the D value (used in the Setchnow equation) for iron, a constituent of naturally occurring geothermal brines, was not known. The effect on silica solubility for a variety of solutes found in geothermal brines was discussed, as was the applicability of the Setchnow equation to determine the solubility of silica in an artificial brine. But that paper contains no discussion of the action of iron on the solubility of silica, nor is any effect on salting out or precipitation proposed for iron.

The problem of silica precipitation in geothermal systems is pervasive in that industry. Methods advanced to combat this problem include adding flocculant to the clarifier/separator. This approach is taught in U.S. Pat. No. 4,874,529 issued to Featherstone et al., which patent is hereby incorporated in full by reference. A second approach is the modification of the geothermal brine process stream pH. This approach is taught in U.S. Pat. No. 4,500,434 issued to Jost et al., which patent is hereby incorporated in full by reference.

It would be advantageous to predict the maximum non-precipitating concentration of silica in an aqueous solution that contains iron. Alternatively, it would be advantageous to predict the point of exceeding the solubility of silica in a solution for each set of conditions found along the brine processing path. But in the case of concentrated solutions having a plurality of solutes, the determination of whether any solute, especially silica, is near saturation is difficult to determine.

SUMMARY OF THE INVENTION

This invention provides a method and an apparatus for predicting whether silica will precipitate from a solution containing iron and other solutes. The system parameters can then be adjusted to minimize scaling. This allows one to use the Setchnow equation for automatic control of a system using a high silica aqueous solution by continuous automatic solving of the Setchnow equation.

An aspect of this invention is a process for controlling the silica content in a geothermal fluid stream from which energy is extracted while controlling the precipitation of scale. First, the concentration of all the dissolved solutes present in the geothermal fluid stream in individual concentrations greater than 1 ppmw is measured. Second, a solution to a Setchnow equation is calculated based on the values measured in the first step to obtain the maximum non-precipitating concentration of silica in the geothermal fluid stream. Third, at least one physical parameter of the geothermal fluid stream is adjusted so as to increase the silica concentration without exceeding the maximum silica concentration value.

A second aspect of this invention is an apparatus for determining the concentration of dissolved silica in an aqueous solution. A means for sensing a physical parameter of the aqueous solution determines that parameter, a means for data processing calculates the solution to the Setchnow equation using the determined parameter, and a system parameter adjustment signal generating means generates an output signal to modify the operation of the system. The physical parameters of the system can be adjusted by referring to the output signal.

A third aspect of this invention is a method for adjusting the physical parameters of a hot brine solution that is nearly saturated in silicon-containing solutes. The physical parameters of the solution are sensed, and the solution to the Setchnow equation is calculated using the parameters selected, and an output signal is produced. The parameters of the solution are then adjusted to maintain maximum solubility of silica solutes.

Naturally occurring geothermal brines that contain substantial concentrations of iron are found, for example, in the Salton Sea, Calif. Now the Setchnow equation can be solved for these naturally occurring brines and cost effective automatic control implemented.

DETAILED DESCRIPTION OF THE INVENTION

Figure 1:
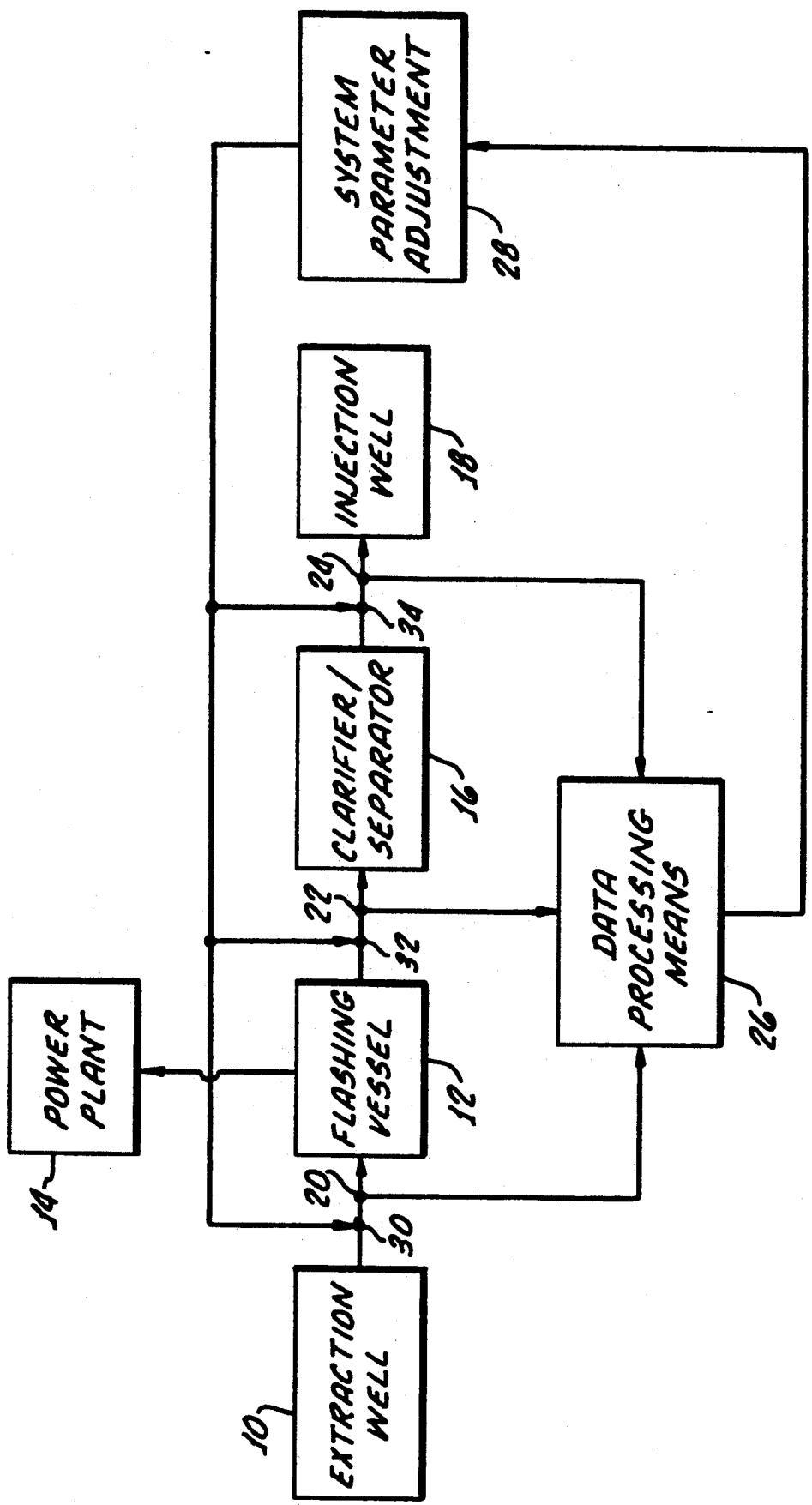
FIG. 1 shows a schematic diagram of a geothermal plant using the control system of this invention.

Referring now to FIG. 1, power is extracted from a geothermal brine in a geothermal power plant. The geothermal brine is extracted from a well 10 that produces hot pressurized geothermal brine. First, the brine is flashed in a flashing vessel 12 where the temperature and pressure of the brine are reduced to produce steam and cool the liquid brine. The steam from flashing vessel 12 is cleaned in a steam cleaner (not shown) and sent to a power plant 14. Before the brine from the flashing vessel 12 can be injected for disposal in an injection well 18 it must be processed to remove enough scale-forming material to result in a clean and cost effective injection. Otherwise, the injection well 18 would rapidly become encrusted with a layer of scale precipitate, resulting in a short-lived injection well. Accordingly, the brine from the flashing vessel 12 is sent to a clarifier/separator 16 to remove as much of the scale-forming material as possible from the brine before injection. Then the brine is pumped to an injection well 18.

The system has a series of interstage parameter determination points between each process step. A first parameter determination point 20, before the flashing vessel, a second parameter determination point 22, after the flashing vessel, and a third parameter determination point 24 before the injection well comprise the interstage parameter determination points. At each interstage parameter determination point in the process, the brine is sampled by a means for sensing a physical parameter of a geothermal brine to determine the silica concentration. In a commercially operating system many parameter determination points are sampled to fully evaluate the system. The silica concentration, c, can be sampled directly by using, for example, a series 5000 Silica Analyzer, made by HACH Inc., Loveland, Colo. If the geothermal brine solution is well characterized, and the concentrations of all the dissolved solutes are well known, then the silica concentration of the brine at a given temperature will be known. In this case a physical parameter sensed can be pressure or temperature, and the silica concentration calculated from the knowledge of this physical parameter.

Although maximum silica solubility (as opposed to silica concentration) was difficult to determine in the presence of many solutes, it can be calculated by solving the Setchnow equation. As more solutes are present in the solution each salt becomes relatively less soluble. Silica solubility is greatly reduced by the recently quantified effect caused by iron which reacts to form the iron silicate scale. The parameters determined at the interstage parameter determination points 20, 22, and 24 are fed into a data processing means 26, for example a computer, to solve the Setchnow equation:

$$\log s = \log s_0 - \Sigma_i(D_i m_i) \quad (equation\ 1),$$

where s is the maximum solubility of silica in the solution of interest at a particular temperature, $s_0$ is the solubility of silica in distilled water at that temperature, $D_i$ is a proportionality constant for a given temperature (hereinafter referred to as the "D value") for each other solute known to be in the solution, and $m_i$ is the molal concentration of the respective solute in the solution. As used herein, all $m_i$ values will correspond to concentrations at least 1.0 ppmw.

The maximum solubility for the amorphous silica in solution may be found by solving the Setchnow equation in a data processing means 26. Data processing means 26 is connected to each of the interstage points. The data processing means 26 is preferably a microprocessor controlled data processor or a minicomputer that would normally be used to control the geothermal power production process. The maximum concentration of silica that can be dissolved in the solution is calculated by finding the appropriate D value for each solute at the temperature of interest. The D values for each solute known to be in the solution in a concentration greater than 1.0 ppmw, including the newly discovered values for Fe(II) and Fe(III), are in an electronic storage device. The data processing means 26 solves the Setchnow equation to provide a value for s, the solubility of silica in the solution of interest.

Data processing means 26 also comprises a system parameter adjustment signal generating means. Once the solubility of silica is known, the data processor calculates the change in the system parameters throughout the system to optimize the operation of the system. The data processing means then generates the system parameter adjustment signal 28, providing the input for automatic devices, such as electrically driven valves. The system parameters can be adjusted at each interstage point in the process, at a first adjustment point 30 before the flashing vessel, at a second adjustment point 32 after the flashing vessel, and at a third system parameter adjustment point 34 before the injection well. It will be realized that the parameter adjusted may be different than the parameter whose value has been determined.

Any system parameter that modifies the solubility of silica can be changed. One option of changing a system parameter is changing the pressure, thereby changing the temperature, by closing or restricting the flow of brine through a valve, at one or more of the adjustment points 30, 32, and 34. The valves are electrically opened or closed by, for example, stepper motors, thereby changing the system parameters, for example, flow rates. The amount of valve adjustment is controlled by the system parameter adjustment signal. Examples of other possible options include modifying the recycle rate of nucleation seed added to the separator/clarifier, adjusting the pH of the system, or modifying the rate of addition of flocculant or dispersant tot he flashing vessel. Other possible modifications to any particular system will suggest themselves as the system is operated.

In a preferred embodiment of this invention, the data processing means 26 calculates the difference between the maximum allowable silica concentration, s, and the silica concentration detected, c, in the solution. Then adjustments to the system can be made depending on whether the difference is positive or negative. If the difference is positive the operating parameters can be adjusted to increase the concentration of silica. For example, if an analysis of the geothermal solution at interstage point 20 shows that more silica can be dissolved in the solution, then a valve at 32 can be opened to allow a reduction in pressure, therefore a reduction in temperature, allowing production of more steam in the flashing vessel. If the difference is negative, the solution is super saturated in silica, and steps are taken to increase the rate of precipitation of silica to ensure that the brine disposed of by injection down hole will create as little scaling down hole as possible. For example, if an analysis of the geothermal solution at interstage point 24 shows a super saturated effluent stream from the clarifier/separator 16, the recycle rate of the seed solution used to nucleate the solid that precipitates is increased. In an actual system both steps given as examples may be taken simultaneously or independently.

The geothermal brine is analyzed to determine the concentrations of all ions and molecules present in concentrations at least 1.0 ppmw dissolved in the solution, since the Setchnow equation cannot be solved without knowing the concentrations of all the dissolved solutes. Each of the solutes dissolved in the aqueous solutions contribute to a "salting out" effect resulting in a reduction of dissolved silica the solution can contain. Salting out is a theoretical model that provides predictive results by assuming that dissolved ions remove water available for the hydration of other dissolved ions. The salting out effect caused by each ion is represented by the proportionality constant (the D value) in the Setchnow equation. In each solution of interest the geothermal brine is analyzed to determine the concentrations of all ions and molecules dissolved in the solution. The effect of each ion is accounted for when the Setchnow equation is calculated.

An example of one naturally occurring geothermal brine is that found near the Salton Sea, Calif. Salton Sea geothermal brines in addition to NaCl, KCl and $CaCl_2$, contain a host of other solutes in lower concentrations. Table 1 presents a typical reservoir brine composition. After sodium, potassium and calcium, the next most abundant metals in the brine are the transition metals, manganese and iron. But no previous studies have provided quantitative values that allow prediction of the effect of manganese or iron on the solubility of amorphous silica. Consequently, the Setchnow equation could not be solved to yield predictive results. Since manganese and iron are relatively significant constituents of Salton Sea brine and are found in siliceous scale deposits (see Table 2), the need for the D values for iron and manganese, which are now available in FIGS. 2, 3, and 4 to solve the Setchnow equation is apparent.

TABLE 1

| TYPICAL SALTON SEA BRINE COMPOSITION (pH ~ 5.5, Eh ~ −200 mV) | |
|---|---|
| Analyte | ppm |
| Ag | 1 |
| As | 10 |
| B | 300 |
| Ba | 190 |
| Ca | 22,700 |
| Cu | 4 |
| Fe | 700 |
| K | 12,300 |
| Li | 165 |
| Mg | 52 |
| Mn | 760 |
| Na | 49,900 |
| Pb | 70 |
| Rb | 51 |
| Sb | 1 |
| $SiO_2$ | 480 |
| Sr | 380 |
| Zn | 280 |
| Br | 85 |
| Cl | 128,400 |
| F | 16 |
| I | 19 |
| $SO_4$ | 105 |
| $CO_2$ | 500 |
| $H_2S$ | 7 |
| $NH_3$ | 375 |
| TDS | 220,600 |

TABLE 2

| TYPICAL SALTON SEA SCALE COMPOSITION as discussed in Example 4 | |
|---|---|
| Mineral Mode | Range (wt %) |
| CaO | 0.5–1.0 |
| $Fe_2O_3$ | 37.0–43.0 |
| $Mn_2O_3$ | 0.5–1.0 |
| $SiO_2$ | 35.0–42.0 |
| $H_2O$ (hydrated) | 12.0–19.0 |

The presence of iron in the geothermal solution tends to complicate predicting the scaling problem. Iron and manganese in Salton Sea geothermal brine are present primarily in the +2 oxidation state. Traces (~5–30 ppm) of ferric ion, Fe(III), are also detected even though these brines are in a somewhat reduced state. If the brine contains mostly Fe(II), it has been observed, but not understood, that the brine oxidizes at least some of the iron to the Fe(III) state. Silica is found to deposit from these brines together with Fe(III) and Fe(II) iron. Fe(III) silicates predominate at higher temperature (>150° C.), while Fe(II) silicates are found increasingly at lower temperatures (<150° C.). Manganese is found in traces in most scales.

Although FIG. 1 refers to a geothermal brine system, this invention can be used in any system where silica scaling is a problem and it is possible to change the operational parameters of the system. For example, systems using aqueous solutions or brines for boiler water, for cooling tower water, for desalination plant feedstock, for solutions used in plating metals or electrolytically recovering metals, and for oil and gas well applications can benefit from this invention.

Figure 2:
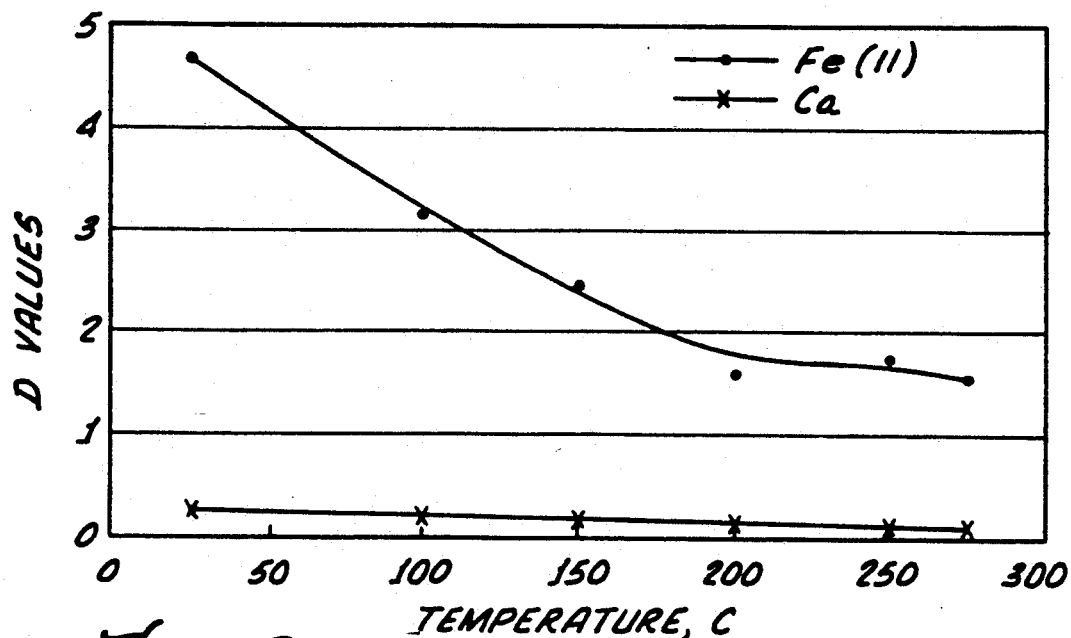
FIG. 2 shows a graphical representation of the newly discovered D values for Fe(II).

Referring to FIG. 2 the D values for Fe(II) are given as a line on a graph of proportionality constants versus temperature. Each D value given as a point at a given temperature is the average of at least four experiments. The D value for Fe(II) is anomalously high compared to the D values listed in the Gallup (1989) for KCl and $CaCl_2$, as well as the earlier known D values for NaCl, $Na_2SO_4$, $MgCl_2$, $MgSO_4$, and $NaNO_3$. The D values for Fe(II) are high because Fe(II) not only encourages a salting out effect but also reacts with the silica, as shown in Reaction 1, resulting in an apparent greatly enhanced salting out effect. The D value for calcium, another +2 valent metal ion, is given for comparison.

Figure 3:
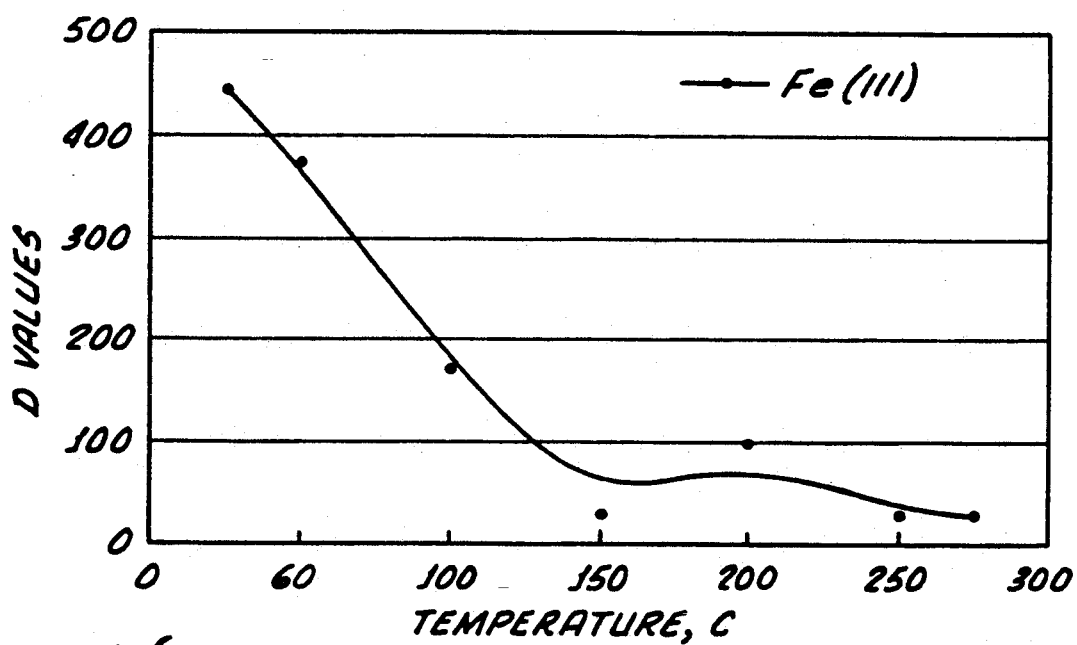
FIG. 3 shows a graphical representation of the newly discovered D values for Fe(III).

Referring to FIG. 3, the D values for Fe(III) are given as a line on a graph of proportionality constants versus temperature. As in the case of Fe(II), the D value for Fe(III) given is the average of at least four experiments, and it is anomalously high compared to the D values listed in the Gallup (1989). The D values for Fe(III) are even higher than the D values for Fe(II).

Figure 4:
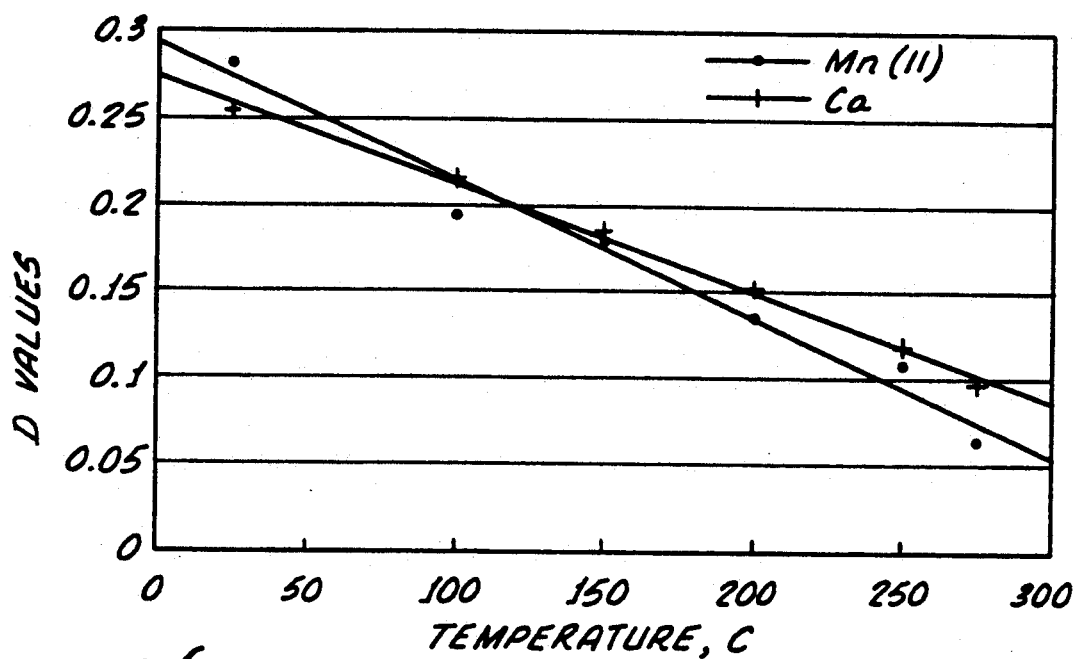
FIG. 4 shows a graphical representation of the newly discovered D values for manganese.

Referring to FIG. 4, the D values for manganese, as $MnCl_2$, are given as a line on a graph of proportionality constants versus temperature. As can be seen the D value for manganese is much less than the D value for iron. The D value for calcium (the same value found on FIG. 2) is given as a comparison. It can be seen that manganese is similar to calcium.

The concentrations of the various ions in a given solution will be known from previous analysis or from continuous on-line analysis. The Setchnow equation can be solved and the limits for silica solubility set. If need be, parameters of the system can be reset to ensure maximum silica solubility. For each different brine or aqueous solution the molalities of the various components are measured and the solution to the Setchnow equation is calculated. The D values of the most commonly found solutes in brines, except for iron, are found in a variety of sources, for example, in Gallup, (1989) and the references cited therein. Other D values needed to calculate the silica solubility in a solution also containing iron are found in FIG. 2, FIG. 3, and FIG. 4 of this disclosure.

EXAMPLES

The invention is further described by the following examples which are illustrative of various aspects of the invention and are not intended as limiting the scope of the invention as defined by the appended claims.

The following Examples all include various data points that have all been calculated using the procedure described below. In Examples 1, 2, and 3 the solubility of silica in the presence iron and manganese ions at a variety of temperatures is described. These examples provide the information needed to solve the Setchnow equation for D (equation 2, below) for the ions Fe(II), Fe(III), and Mn(II). The information shown graphically in FIGS. 2, 3, and 4 can then be derived. In example 4 the solubilities of silica and total iron in a scale taken from a commercially operated geothermal power plant are described. In example 5 the solubilities of amorphous silica in the artificial brine of Gallup (1989) are discussed. In example 6 the solubilities of silica (a) in pure water, (b) as predicted in Gallup (1989), (c) as predicted from this study, and (d) as compared to actual silica solubility found in naturally occurring geothermal brines are contrasted.

The D values represented in FIGS. 2, 3, and 4 can be calculated from the tabulated information in the Examples. The Setchnow equation is solved for unknown D. The concentration of pure silica at the temperatures listed is found in Example 1. The values of silica solubility and iron or manganese solubility are given in tables 3, 4, and 5. The Setchnow equation can then be solved in the form:

$$D_i = \frac{\log s_0 - \log s}{m_i} \quad \text{(equation 2)}$$

The D values obtained are then averaged for the different concentrations of solute (as in Example 2) and the average values plotted against temperature to yield the graphs shown in the figures. It will, of course, be realized that the data tabulated in the examples represent only one data point for each D value, whereas the graphical information in the Figures is an average of 4 or 5 different data sets.

Procedure

This is the procedure used to determine the solubilities of silica in the presence of other solutes for the Examples which follow. Each data point in each of the following tables represents at least one experimental run of this procedure.

Laboratory studies of silica solubility were conducted in a 1 L Hastelloy C-276 autoclave (Autoclave Engineers, Erie, Pa.). Approximately 7 grams of reagent grade silicic acid (Examples 1-3, 5, and 6) or scale collected from the field (Examples 4, and 6) were washed according to the procedure of Marshall, W. L. ("Amorphous silica solubilities I. Behavior in aqueous sodium nitrate solutions; 25°-300° C., 0-6 molal."; *Geochim. Cosmochim. Acta* 44, 925-931. (1980)) to obtain small uniform particles for study. The solid to be studied was placed into the autoclave together with approximately 500 mL of the desired solvent. The head space in the autoclave was purged for several minutes and pressure tested with pre-purified nitrogen.

Reagent grade salts of other cations were employed throughout the metal addition studies. Ferrous chloride solutions were contaminated with traces of Fe(III) ions that were reduced to the Fe(II) state by adding one drop of 6% ammonium thioglycolate (reducing agent) solution.

The mixtures were heated to the desired temperature with stirring (~250 rpm). After equilibration at each temperature for a minimum of 3 hours, a 10 mL sample was withdrawn from a sample port cooled with ice water. The aliquot was immediately filtered (0.45 micron Millipore), fixed with dilute ultrapure nitric acid solution (~1 N) and analyzed for dissolved silica and metals of interest by inductively-coupled plasma (ICP) spectroscopy.

In all experiments, silica and metal concentrations were measured at temperatures during heating and cooling of the autoclave to provide at least two analyses per temperature setting. Hysteresis proved acceptable as the concentrations from the heating and cooling cycles were averaged yielding reproducibility of ~2% for a given temperature (+2° C). Ferric ion in the samples was distinguished from total iron by careful colorimetric analysis employing standard thiocyanate complexation techniques. Solids remaining at the conclusion of the experiments were analyzed by ICP and Mössbauer spectroscopy.

Example 1

In this Example silica solubility is determined as a function of temperature in pure water and in the presence of Fe(II). Silica solubility in the presence of calcium is shown for comparison.

Amorphous silica solubility was examined at several temperatures in a solution containing 0.02 molal (m) $FeCl_2$. This concentration of Fe(II) approaches the level of total iron present in the Salton Sea geothermal brine. Included for comparison are silica solubility data obtained in pure water. The results of these studies are shown in Table 3. Silica solubility in both the Fe(II) and calcium solutions was depressed compared to pure water.

Calcium chloride, a divalent metal salt, exhibits a hydration number of 12. Therefore, $FeCl_2$, a divalent metal salt, would be expected to exhibit a similar "salting out" effect compared to $CaCl_2$. However, $FeCl_2$ depresses silica solubility much more than $CaCl_2$. The apparent cation hydration number, h, for Fe(II) was calculated by the method of Fournier and Marshall, ("Calculation of amorphous silica solubilities at 25° to 300° C. and Apparent Cation Hydration Numbers in Aqueous Salt Solutions Using the Concept of Effective Density of Water."; *Geochim. Cosmochim. Acta* 47, 587-596. (1983)). The data from these experiments yield a value of h at 25° C. exceeding 1500. Clearly 1500 waters of hydration around each Fe(II) ion in solution is an unreasonably high number.

TABLE 3

THE MOLAL SOLUBILITY OF AMORPHOUS SILICA IN 0.02 m $FeCl_2$, 0.02 m $CaCl_2$ AND PURE WATER

| Temperature, °C. | $FeCl_2$ | | $CaCl_2$ | Pure $H_2O$ |
|---|---|---|---|---|
| | $SiO_2$, m | Fe, m | $SiO_2$, m | $SiO_2$, m |
| 25 | 0.00077 | 0.0189 | 0.00220 | 0.00217 |
| 50 | 0.00153 | 0.0186 | 0.00379 | 0.00385 |
| 100 | 0.00577 | 0.0184 | 0.00668 | 0.00675 |
| 150 | 0.00949 | 0.0183 | 0.0108 | 0.0109 |
| 200 | 0.0146 | 0.0188 | 0.0156 | 0.0157 |
| 250 | 0.0190 | 0.0180 | 0.0209 | 0.0211 |
| 275 | 0.0213 | 0.0175 | 0.0238 | 0.0240 |

$FeCl_2$ depressed silica solubility beyond what would have been expected based on the previously known results for calcium. This indicates that another phenomenon in addition to "salting out" is involved in the $FeCl_2$—$SiO_2$ system. During the experiments with $FeCl_2$, the concentration of iron in solution was observed to decrease compared to the 0.02 m initially present (see Table 3). The solid remaining in the autoclave at the end of each experiment that included iron had turned from the normal white color characteristic of excess amorphous silica to a brown color. The solid was analyzed and found to contain up to 5 wt % iron. Mössbauer spectroscopic examination of the solids showed the presence of both Fe(II) and Fe(III) iron in what appears to be a silicate phase. No simple iron chlorides, iron oxides, (for example, magnetite or hematite), or iron oxyhydroxides (for example, goethite) in the solid were detected. Thus, experimental evidence suggests that $FeCl_2$ reduces the apparent solubility of amorphous silica by a precipitation reaction.

Example 2

In this example the solubility of silica at different temperatures in the presence of different concentrations of Fe(III) is determined.

The effect of $FeCl_3$ on amorphous silica solubility was investigated over the temperature range, 25°–275° C. Three different concentrations of $FeCl_3$ were examined 0.00045 m, 0.0045 m and 0.045 m. The pH of the stock solutions were not neutralized before being placed in contact with silicic acid powder in the autoclave. The respective starting values for pH in these solutions were 3.1, 2.4 and 1.8. The results of the silica solubility studies in $FeCl_3$ solutions are shown in Table 4. As observed in the $FeCl_2$ case, silica solubilities were significantly depressed, iron was lost from solution, and the resultant solids remaining in the autoclave at the conclusion of the tests appeared to be iron silicate.

TABLE 4

THE MOLAL SOLUBILITY OF AMORPHOUS SILICA IN $FeCl_3$ SOLUTIONS FROM 25–275° C.

| Temp., °C. | 0.00045 m | | 0.0045 m | | 0.045 m | |
|---|---|---|---|---|---|---|
| | $SiO_2$, m | Fe, m | $SiO_2$, m | Fe, m | $SiO_2$, m | Fe, m |
| 25 | 0.00065 | 0.00011 | 0.00047 | 0.0031 | 0.00033 | 0.031 |
| 50 | 0.00136 | 0.00010 | 0.00118 | 0.0029 | 0.00095 | 0.0016 |
| 100 | 0.00428 | 0.00007 | 0.00357 | 0.0018 | 0.00250 | 0.00072 |
| 150 | 0.0102 | 0.00007 | 0.00874 | 0.00066 | 0.00820 | 0.00028 |
| 200 | 0.0166 | 0.00005 | 0.00141 | 0.00041 | 0.0126 | 0.00011 |
| 250 | 0.0196 | 0.00004 | 0.0187 | 0.00016 | 0.0162 | 0.00013 |
| 275 | 0.0223 | 0.00004 | 0.0214 | 0.00004 | 0.0192 | 0.00013 |

Amorphous silica solubilities at a given temperature decreased with increasing initial concentration of $FeCl_3$. With more Fe(III) iron available, it appears that more iron silicate was generated. Comparison of the results given in Table 4 with the $FeCl_2$ results discussed in Example 1 indicates that $FeCl_3$ depresses the silica solubility to a greater extent than $FeCl_2$ Fe(III) likely exhibits a higher cation hydration number, h, than Fe(II).

Example 3

In this Example the solubility of silica is determined as a function of temperatures in the presence of manganese. Silica solubility in the presence of calcium is shown for comparison.

Manganese is a common transition metal found in Salton Sea brine. However, in contrast to iron, very little manganese is deposited in scales obtained from the Salton sea geothermal field. Manganese is present in the brine in primarily the +2 oxidation state. Amorphous silica solubility in the presence of dilute $MnCl_2$ solution (0.02 m) is presented in Table 5. This concentration approaches that present in Salton Sea geothermal brine. The data from this experiment suggest that manganese affects silica solubility in a manner similar to calcium. Since calcium is known to act primarily as a "salting out" agent, this suggests that manganese also acts primarily as a "salting out" agent rather than a precipitant of amorphous silica. The data indicate that $MnCl_2$ exhibits a hydration number, h, of 11 (calculated as in Example 1). Based on the data for calcium, one would expect that amorphous silica will "salt out" to about the same degree as calcium, which has a hydration number, h, of 12. Included in Table 6 are data for $CaCl_2$. These data are very similar to those obtained for $MnCl_2$.

TABLE 5

MOLAL SOLUBILITY OF AMORPHOUS SILICA IN 0.02 m $MnCl_2$ FROM 25–275° C.

| Temp., °C. | 0.02 m $MnCl_2$ | | 0.02 m $CaCl_2$ |
|---|---|---|---|
| | $SiO_2$, m | Mn, m | $SiO_2$, m |
| 25 | 0.00201 | 0.020 | 0.00220 |
| 50 | 0.00375 | 0.019 | 0.00379 |
| 100 | 0.00664 | 0.018 | 0.00668 |
| 150 | 0.0105 | 0.020 | 0.0108 |
| 200 | 0.0157 | 0.018 | 0.0156 |
| 250 | 0.0210 | 0.019 | 0.0209 |
| 275 | 0.0236 | 0.021 | 0.0238 |

Example 4

In this example scale solubility as a function of temperature is presented for scale removed from a geothermal plant.

Scales deposited from Salton Sea geothermal brine at 200° C. were examined in the laboratory autoclave. These scales exhibited a composition similar to that shown in Table 2, and Mössbauer spectroscopy showed the presence of Fe(III) iron only. The scale solubility was determined in pure water. Scale solubilities varied slightly from sample to sample, probably due to minor variations in composition. Averaged values for silica and iron from these experiments are given in Table 6.

Fe(III) silicate scale is much less soluble than pure amorphous silica, (values for pure amorphous silica are found in Table 3). This indicates again that a chemical reaction with Fe(III) is depressing the silica solubility beyond what would have been expected from the simple "salting out" model. For reasons that are not clear, the silica and iron fractions were observed to dissolve in different manners.

TABLE 6

MOLAL SOLUBILITY OF FERRIC SILICATE SCALE DEPOSITED FROM SALTON SEA GEOTHERMAL BRINE

| Temperature, °C. | $SiO_2$, m | Fe, m |
|---|---|---|
| 25 | 0.00018 | 0.00039 |
| 50 | 0.00039 | 0.00082 |
| 100 | 0.00061 | 0.00098 |
| 150 | 0.00428 | 0.00063 |
| 200 | 0.0132 | 0.00079 |
| 250 | 0.0187 | 0.0011 |
| 275 | 0.0196 | 0.0011 |

Example 5

In this Example, silica solubility as a function of temperature is presented for the artificial brine of Gallup (1989). The change in silica solubility upon adding different metal ions to that brine is measured.

Using the new data herein disclosed, one can add upon the predictive capability of the original model of Gallup (1989). The solubility of amorphous silica was measured in a simple synthetic brine that included only sodium, potassium, calcium and chloride. The solubility of silica was also measured in four other synthetic brines of the same composition as the simple synthetic brine, but further containing respectively (a) Fe(II), (b) Fe(III), (c) both Fe(II) and Fe(III), and (d) both Fe(II) and Fe(III) together with manganese. Artificial brine (d) more closely approximates the naturally occurring Salton Sea geothermal brine compared to the simpler systems, because the transition metal salts that exhibit both precipitation and "salting out" effects are incorporated into the model. In Table 7 the results of selected experiments conducted with the more complex solute mixture are presented. For comparison, Table 7 includes previous experimental and calculated (model) results obtained for the Na-K-Ca-Cl system. In these experiments, the addition of either soluble Fe(II) or Fe(III) or both were always observed to decrease silica concentration, suggesting formation of an iron silicate precipitate. The other cations remained stable in solution.

TABLE 7

MOLAL SOLUBILITY OF AMORPHOUS SILICA IN A SERIES OF SYNTHETIC BRINES***

| Temp., °C. | Model Na—K—Ca | Measured Na—K—Ca | a* | b** | c*** | d**** |
|---|---|---|---|---|---|---|
| 25 | 0.00099 | 0.00093 | 0.00090 | 0.00076 | 0.00088 | 0.00090 |
| 100 | 0.00359 | 0.00338 | 0.00338 | 0.00251 | 0.00325 | 0.00310 |
| 150 | 0.00639 | 0.00626 | 0.00535 | 0.00530 | 0.00594 | 0.00620 |
| 200 | 0.0101 | 0.00983 | 0.00862 | 0.00890 | 0.00981 | 0.00878 |
| 250 | 0.0149 | 0.0143 | 0.0118 | 0.0129 | 0.0137 | 0.0126 |
| 275 | 0.0155 | 0.0149 | 0.0128 | 0.0141 | 0.0145 | 0.0139 |

*Na, K, Ca, Fe(II), and Cl
**Na, K, Ca, Fe(III), and Cl
***Na, K, Ca, Fe(II), Fe(III), and Cl
****Na, K, Ca, Fe(II), Fe(III), Mn, and Cl
*****All brines contained chloride salts of Na, K, and Ca respectively in the following concentrations: 2.33 m NaCl, 0.32 m KCl, and 0.57 m $CaCl_2$. Brines a, c, and d also contained 0.02 m $FeCl_2$. Brines b, c, and d also contained 0.0005 m $FeCl_3$. Brine d also contained 0.02 m $MnCl_2$.

Example 6

In this Example the solubilities of silica as (a) predicted by this work, (b) predicted by Gallup(1989), and (c) observed in the field are compared.

The effect of adding manganese and iron salts to the Na-K-Ca simple synthetic brine discussed in Example 5 slightly depresses the silica solubility lower than reported for the Na-K-Ca-Cl system. These data, when averaged (see Table 8), yield silica solubilities that accurately predict the actual silica concentrations at a given temperature for brine produced from the Salton Sea field. The data in Table 8 show how the complex brine system model containing iron and manganese, when extrapolated to the field brine salinity, more closely predicts the actual value measured in the field than the earlier model of Gallup (1989). Specifically, the data in Table 8 below are more predictive of the silica solubilities actually found in geothermal brines in the field than is Gallup 1989. This is demonstrated by the data in Table 9 which comes from an actual field brine of higher total salinity than the experimental brines. It is obtained at 109° C. and is stabilized with respect to scale deposition in a clarifier.

TABLE 8

AVERAGE MOLAL SOLUBILITIES OF AMORPHOUS SILICA IN COMPLEX BRINES

| Temp., °C. | This Study Ave. $SiO_2$, m | Pure Water $SiO_2$, m | Gallup (1989) $SiO_2$, m |
|---|---|---|---|
| 25 | 0.00086 | 0.00217 | 0.00093 |
| 100 | 0.00306 | 0.00675 | 0.00338 |
| 150 | 0.00570 | 0.0109 | 0.00626 |
| 200 | 0.00903 | 0.0157 | 0.00983 |
| 250 | 0.0128 | 0.0211 | 0.0143 |
| 275 | 0.0138 | 0.0240 | 0.0149 |

TABLE 9

COMPARISON OF SILICA CONCENTRATIONS OBSERVED IN THE FIELD, PREDICTED BY GALLUP (1989), AND PREDICTED BY THE PRESENT INVENTION

| Temp °C. | $SiO_2$, m | Observation or Prediction |
|---|---|---|
| 109 | 0.00272 | Observed in the Field |
| 109 | 0.00282 | Predicted using Na—K—Ca—Cl Model (Gallup (1989) |
| 109 | 0.00273 | Predicted using this Study and the new Mn and Fe D values (FIGS. 2, 3, and 4) |

The complex brine is much more predictive of actual silica solubilities than the less complex brine system model incorporating only Na-K-Ca-Cl developed earlier (Gallup (1989)). Notice that the invention allows very accurate prediction of the maximum solubility of silica found in a geothermal plant. The greater degree of predictability now allows one to automatically control the flow of a solution containing both iron and silica as described in FIG. 1.

With the new D values generated by the data in the Examples and graphically in FIGS. 2, 3, and 4, one can provide for automatic control of, for example, a geothermal plant as shown in FIG. 1. The silica concentration of the brine can be accurately compared to the maximum non-precipitating concentration of silica for that temperature in the presence of other ions, especially including Fe(II) and Fe(III). The operating conditions of the plant can be changed to increase silica solubility at, for example, the flashing stage. In the clarifier/separator stage, for example, the solution can be monitored to ensure that the silica concentration in the solution does not exceed the maximum non-precipitating solubility for silica, in other words, to ensure that the solution is not super-saturated.

Although this invention has been primarily described in conjunction with references to the examples and the preferred embodiments thereof, it is evident that many alternatives, modifications and variations will be apparent to those skilled in the art in light of the foregoing description. Accordingly, it is intended that the spirit and scope of the appended claims embrace all such alternatives, modifications and variations.

I claim:

1. A process for controlling the silica content in a geothermal fluid stream from which energy is extracted while controlling the precipitation of scale comprising:
   (a) measuring the concentration of all the dissolved solutes present, including the concentration of silica, in the geothermal fluid stream in individual concentrations greater than 1.0 ppmw;
   (b) calculating the maximum solubility of silica that can exist in the solution by solving for s in a Setchnow equation;

$$\log s = \log s_0 - \Sigma_i(D_i m_i),$$

where s is the maximum solubility of silica in the solution of interest at a particular temperature, $s_0$ is the solubility of silica in distilled water at that temperature, $D_i$ is a proportionality constant for a given temperature each other solute known to be in the solution, and $m_i$ is the molal concentration of the respective solute in the solution based on the values measured in step (a) to obtain the maximum nonprecipitating concentration of silica in the geothermal fluid stream; and
   (c) adjusting a physical parameter of the geothermal fluid, selected from the group of physical parameters consisting of temperature, pressure, recycle seed rate, and flow rate, so as to increase the silica concentration in the solution without exceeding the maximum silica concentration value of the solution.

2. The process of claim 1 wherein silica concentration is measured by a silica analyzer.

3. The process of claim 1 wherein the Setchnow equation is solved for all solutes in solution including Fe(II) and Fe(III).

4. The process of claim wherein the parameter adjusted in system pressure.

5. The process of claim 1 wherein the parameter adjusted is recycle seed rate to a clarifier/separator.

6. An apparatus for automatically adjusting physical parameters of an aqueous solution containing silica and iron comprising:
   means for measuring the value of a physical parameter related to the concentration of silica and another related to the concentration of iron of an aqueous solution;
   means for data processing using the value of the physical parameter to calculate a solution to a Setchnow equation:

$$\log s = \log s_0 - \Sigma_i(D_i m_i),$$

where s is the maximum solubility of silica in the solution of interest at a particular temperature, $s_0$ is the solubility of silica in distilled water at that temperature, $D_i$ is a proportionality constant for a given temperature representing the salting out effect caused by each other solute, including Fe(II) and Fe(III), known to be in the solution, and $m_i$ is the molal concentration of the respective solute in the solution, a table of D values $m_i$ values for each solute, known to be dissolved int he aqueous solution stored in electronically recoverable form relating the measured concentrations of solution components to the maximum silica solubility calculated from the Setchnow equation to produce an output signal; and
   means for adjusting a physical parameter of the geothermal fluid, selected from the group of physical parameters consisting of temperature, pressure, flow rate, and recycle seed rate, of the aqueous solution based on the output from the means for data processing to change silica solubility.

7. The apparatus of claim 6 wherein the means for measuring comprises a temperature detecting device.

8. The apparatus of claim 6 wherein the means for measuring is a pressure sensitive device.

9. The apparatus of claim 6 wherein the means for data processing is a microprocessor chip.

10. A method for adjusting physical parameters of an aqueous solution containing less than a saturated concentration of amorphous silica, comprising:
    measuring a physical parameter related to the concentration of silica in the solution and producing a value;
    calculating the maximum solubility of silica that can exist in the solution by solving for s in a Setchnow equation:

$$\log s = \log s_0 - \Sigma_i(D_i m_i),$$

where s is the maximum solubility of silica in the solution of interest at a particular temperature, $s_0$ is the solubility of silica in distilled water at that temperature, $D_i$ is a proportionality constant for a given temperature representing the salting out effect caused by each other solute, known to be in the solution, and $m_i$ is the molal concentration of the respective solute in the solution using the value of the measured physical parameter and producing an output signal; and
    adjusting a physical parameter of the aqueous solution, selected from the group of physical parameters consisting of temperature, pressure, flow rate, and recycle seed rate, based on the output signal to change silica solubility.

11. The method of claim 10 wherein the sensing step comprises measuring the temperature of the aqueous solution.

12. The method of claim 10 wherein the measuring step comprises measuring the pressure of the aqueous solution.

13. The method of claim 10 wherein the calculating step comprises determining the D values of the Setchnow equation by referring to a table of D values, including the values for Fe(II) and Fe(III), stored in an electronic memory.

14. The method of claim 10 wherein the parameter adjusted increases silica solubility.

15. The method of claim 10 wherein the parameter adjusted decreases silica solubility.

16. The method of claim 15 wherein decreasing silica solubility increases the rate of silica precipitation.

17. The method of claim 10 wherein the parameter comprises a flow rate.

18. A method for adjusting physical parameters of a flowing stream of a geothermal brine solution processing system containing less than a saturated concentration of amorphous silica, comprising:
   measuring the concentration of silica of the geothermal brine solution;
   calculating, with a data processing device, the maximum solubility of silica that can exist in the geothermal brine by solving for s in a Setchnow equation:

$$\log s = \log s_0 - \Sigma_i(D_i m_i),$$

where s is the maximum solubility of silica in the solution of interest at a particular temperature, $s_0$ is the solubility of silica in distilled water at that temperature, $D_i$ is a proportionality constant for a given temperature representing the salting out effect caused by each other solute known to be in the solution, and $m_i$ is the molal concentration of the respective solute in the solution and producing an output signal; and
   adjusting a physical parameter of the geothermal brine, selected from the group of physical parameters consisting of temperature and pressure, of the geothermal brine solution based on the output signal to change silica solubility.

19. The method of claim 18 wherein the data processing device includes an electronic connection with a means for measuring the concentration of silica.

20. The method of claim 18 wherein the parameter adjusted is a flow rate.

21. The method of claim 20 wherein the flow rate adjustment increases silica solubility.

22. The method of claim 18 wherein the parameter adjusted is seed recycle rate in a clarifier.

23. The method of claim 22 wherein the seed recycle rate adjustment decreases silica solubility.

24. The method of claim 23 wherein decreasing silica solubility increases the rate of silica precipitation.

25. The method of claim 18 wherein the parameter adjusted is reaction well solids concentration in a clarifier.

26. The method of claim 25 wherein the parameter adjusted decreases silica solubility.

27. The method of claim 26 wherein decreasing silica solubility increases the rate of silica precipitation.

28. A method for controlling precipitation of a dissolved silicon-containing constituent from an aqueous solution stream also containing iron constituents and manganese constituents comprising:
   measuring the concentrations of said dissolved silicon-containing, iron-containing and manganese-containing constituents at an interstage parameter determination point;
   calculating a precipitation concentration of silica at said initial conditions above which said silicon-containing constituent will start to precipitate;
   generating a signal; and
   changing a process parameter of the aqueous solution, selected from the group of physical parameters consisting of temperature and pressure, in response to the generated signal if said precipitation concentration exceeds a threshold concentration.

29. The method of claim 28 wherein said measuring step also comprises measuring an initial temperature and a downstream temperature.

30. The method of claim 29 wherein said calculating compares the initial temperature and the downstream temperature to generate the parameter adjustment signal.

31. The method of claim 30 wherein said data processing is based upon solving for s, the maximum concentration of silica allowed in a given solution, in a Setchnow equation;

$$\log s = \log s_0 - \Sigma_i(D_i m_i),$$

where s is the maximum solubility of silica in the solution of interest at a particular temperature, $s_0$ is the solubility of silica in distilled water at that temperature, $D_i$ is a proportionality constant for a given temperature representing the salting out effect caused by each other solute known to be in the solution, and $m_i$ is the molal concentration of the respective solute in the solution.

32. The method of claim 28 wherein said solution stream comprises an aqueous geothermal stream.

33. The method of claim 28 wherein the interstage determination point is after a flashing stage.

34. The method of claim 28 wherein the interstage determination point is after a separator/clarifier stage.

35. A method for controlling precipitation of a dissolved silicon-containing constituent from an aqueous solution stream at an initial process condition in a process wherein silicon-containing constituents precipitate in later processing steps at different process conditions, said solution also comprising a dissolved iron-containing constituent, said method comprising:
   measuring the concentration of said dissolved silicon-containing and iron-containing constituents at said initial process condition;
   calculating a saturated concentration of said dissolved silicon-containing constituent;
   subtracting said measured concentration of silicon-containing material from said saturated concentration to produce a precipitation potential concentration; and
   changing a process parameter of the aqueous solution, selected from the group of physical parameters consisting of temperature and pressure, if said precipitation potential concentration exceeds a threshold;
   wherein said calculating of said saturated concentration of silicon-containing constituent is based upon the tendency of ions dissolved in solution to decrease the solubility of silicon-containing components.

* * * * *

UNITED STATES PATENT AND TRADEMARK OFFICE
CERTIFICATE OF CORRECTION

PATENT NO. : 5,246,593

DATED : September 21, 1993

INVENTOR(S) : Darrell L. Gallup

It is certified that error appears in the above-identified patent and that said Letters Patent is hereby corrected as shown below:

Claim 1, column 13, line 32, replace ";" with -- : --.

Claim 1, column 13, line 39, after "temperature" insert -- representing the salting out effect caused by --.

Claim 4, column 13, line 58, after "claim" insert -- 1 --.

Claim 4, column 13, line 59, replace "in" with -- is --.

Claim 6, column 14, line 16, replace "int he" with -- in the --.

Claim 31, column 16, line 22, replace ";" with -- : --.

Signed and Sealed this

Nineteenth Day of April, 1994

Attest:

BRUCE LEHMAN

*Attesting Officer*  *Commissioner of Patents and Trademarks*